United States Patent [19]

Boosen

[11] 4,133,827
[45] Jan. 9, 1979

[54] PROCESS FOR THE PRODUCTION OF α-CYANO-γ-HALOACETOACETIC COMPOUNDS

[75] Inventor: Karl-Josef Boosen, Erlach, Switzerland

[73] Assignee: Lonza Ltd., Gampel, Switzerland

[21] Appl. No.: 796,808

[22] Filed: May 13, 1977

[30] Foreign Application Priority Data

May 13, 1976 [CH] Switzerland .................. 6017/76

[51] Int. Cl.² .............. C07C 120/00; C07D 295/18; C07D 211/16
[52] U.S. Cl. .............. 260/465.4; 260/465 D; 544/163; 546/245
[58] Field of Search .......... 260/465.4, 465 D, 293.86; 544/163

[56] References Cited
PUBLICATIONS

Migrdichian, The Chemistry of Organic Cyanogen Compounds, 1947, p. 112.
Houben-Weyl, Methoden der Organischen Chemie, 1952, Band VIII, Sauerstoffverhindgungen III, pp. 316-317.

Primary Examiner—Joseph Paul Brust
Attorney, Agent, or Firm—Fisher, Christen & Sabol

[57] ABSTRACT

Process for the production of an α-cyano-γ-halo acetoacetic compound of the general formula:

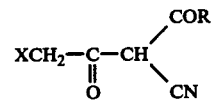

wherein X is halogen, R is $-NR_1R_2$, $-NHR_3$ or $-O-R_4$, $R_1$ and $R_2$ are each alkyl having 1 to 18 carbon, or $R_1$ and $R_2$ form a morpholino or piperidino heterocyclic group with the N in $-NR_1R_2$, $R_3$ is alkyl having 1 to 18 carbon atoms or aryl, and $R_4$ is alkyl having 1 to 10 carbon atoms or aryl. The process includes reacting an alkali metal alcoholate and the haloacetoacetic compound of the formula:

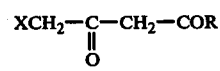

wherein X and R are the same as defined above. A metal salt of the haloacetoacetic compound of the formula:

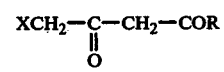

wherein X and R are the same as defined above and wherein the metal in the metal salt is an alkali metal, results. Then the metal salt of the haloacetoacetic compound and a halo cyanogen in an inert solvent are reacted.

14 Claims, No Drawings

4,133,827

PROCESS FOR THE PRODUCTION OF α-CYANO-γ-HALOACETOACETIC COMPOUNDS

BACKGROUND OF THIS INVENTION

1. Field of this Invention

This invention relates to the production of α-cyano-γ-haloacetoacetic compounds.

2. Prior Art

α-cyano-γ-haloacetoacetic compounds, especially α-cyano-γ-haloacetoacetic esters, have been produced from cyanoacetic esters and haloacetyl halides. Thus, for example, Benary in Ber. 41, 2399 (1908) describes the production of α-cyano-γ-chloroacetoacetic ethyl ester from cyanoacetoacetic ethyl ester and chloroacetyl chloride, with a yield of about 55 to 60 percent. However, such method has a number of disadvantages, among them being the particularly cumbersome and tedious processing which is involved, and which has prevented hitherto any larger usage of the synthetically valuable compounds.

BROAD DESCRIPTION OF THIS INVENTION

An object of this invention is to provide an improved process for the production of certain α-cyano-γ-haloacetoacetic compounds. Other objects and advantages of this invention are set out herein or are obvious herefrom to one ordinarily skilled in the art.

The objects and advantages of this invention are achieved by the process of this invention.

This invention is a process for the production of α-cyano-γ-haloacetoacetic compounds of the general formula:

$$XCH_2-\underset{\underset{O}{\|}}{C}-CH\overset{COR}{\underset{CN}{\diagdown}}$$

wherein X is halogen, R is $N(R_1\ R_2)$, $NH-R_3$ or $O-R_4$, $R_1$ and $R_2$ are each alkyl having 1 to 18 carbon atoms, $R_1$ and $R_2$ (i.e., $-NR_1\ R_2$) is a morpholino or piperidino heterocyclic group, $R_3$ is alkyl having 1 to 18 carbon atoms or aryl and $R_4$ is alkyl having 1 to 10 carbon atoms or aryl.

The process of this invention involves metal salts of haloacetoacetic compounds of the general formula:

$$XCH_2-\underset{\underset{O}{\|}}{C}-CH_2-COR$$

wherein X and R are the same as described above, in a inert solvent or solvents with a halogenated cyanogen.

Examples of useful alkyl groups are methyl, ethyl, 2-butyl, tertiary butyl, 1-pentyl, 1-hexyl, 1-propyl, 2-propyl, 1-butyl, 2-methyl-1-butyl, neopentyl, 3-methyl-1-butyl, 2-pentyl, 2-octyl, 3-pentyl, 2-methyl-2-butyl, 3-methyl-2-butyl, 2-methyl-1-pentyl, 2-ethyl-1-butyl, 3-methyl-1-pentyl, isohexyl, 4-methyl-2-pentyl, 2-hexyl, 1-octyl, 2-methyl-3-pentyl, n-heptyl, 2-methyl-2-pentyl, 2,2-dimethyl-3-butyl, 3-hexyl, 3-methyl-3pentyl, 2,3-dimethyl-1-butyl, 2,3-dimethyl-2-butyl, 2,4-dimethyl-3-pentyl, 2,4-dimethyl-1-pentyl, 1-nonyl, 1-decyl, 1-undecyl, 1-dodecyl, 1-tridecyl, 1-tetradecyl, 1-pentadecyl, 1-hexadecyl, 2-heptadecyl and 1-octadecyl. $R_1$ and $R_2$ can be the same or different alkyl groups.

Examples of useful aryl groups are phenyl, benzyl (alkaryl), α-naphthyl and β-naphthyl.

Sodium, potassium, rubidium, thallium and mono- and bivalent copper salts can be used as the metal salt. Preferably sodium salts are used as the metal salt.

The haloacetoacetic compounds can have fluorine, chloride, bromine or iodine, preferably chlorine or bromine as the halogen component (i.e., X). Suitable halo cyanogens are cyanogen fluoride, cyanogen chloride and cyanogen bromide; preferably cyanogen chloride is used.

A suitable inert solvent is an alcohol, toluene, benzene or ether. Preferably an alcohol is used from which the alcoholate, which is needed for the production of the metal salts, was prepared. The metal salt of the ester reacts more quickly with the halocyanogen compound than with alcohol. Whenever it is a matter of a Cu— or Tl— salt being used, preferably toluene or benzene is used as the inert solvent.

The reaction takes place according to the general formula:

$$XCH_2-\underset{\underset{O^{\ominus}}{|}}{C}=CHCOR\ M^{\oplus} + YCN \longrightarrow$$

$$XCH_2-\underset{\underset{O}{\|}}{C}-CH\overset{COR}{\underset{CN}{\diagdown}} + MY.$$

wherein:
R is the same as defined above
X is F, Cl Br or I; preferably Cl or Br $M^+$ is $Na^+$, $K^+$, $Rb^+$, $Tl^+$, $Cu^+$ or $Cu^{2+}$; preferably $Na^+$ for the esters; preferably $Cu^+$ for the amides.
Y is F, Cl or Br; preferably Cl The production according to this invention of the α-cyano-γ-haloacetoacetic compounds is carried out in such a way that for example, the ester or the amide is dissolved in benzene or toluene and the solution is shaken up to quantitative conversion with an aqueous metal salt solution, for example, $Cu(OOCCH_3)_2$, or by first dissolving the calculated quantity of an alkali metal, for example, sodium, in an alcohol and by reacting the alcoholate subsequently formed with the γ-haloacetoacetic compound, whereby the salt of the compound and alcohol are formed.

Without isolating the metal salt a stoichiometric quantity, possibly a slight excess, of the halo cyanogen may be inserted into the reaction mixture at temperatures of −10° to +40° C.

The end product may be obtained in pure form by extraction and then evaporation of the extraction agent.

α-cyano-γ-haloacetoacetic compounds have four functional groups per molecule and are thus accessible to a countless number of reactions. These compounds represent very valuable intermediate products for the production of pharmaceutical, pesticides, dyes and special heterocyclic compounds.

For example, the α-cyano-γ-haloacetoacetic ester may be used according to Swiss Pat. No. 533,778 for the production of pyrolinones.

DETAILED DESCRIPTION OF THIS INVENTION

As used herein, all weights, ratios and percentages are on a weight basis unless otherwise stated or unless

EXAMPLE 1

4.7 gm. (0.205 gm-At) of Na was dissolved in 60 ml of absolute EtOH to produce sodium ethylate. After cooling to 0° to 5° C., 16.4 gm. (0.1 mole) of γ-chloroacetoacetic acid ethyl ester was added drop by drop and subsequently 6.1 gm of ClCN was introduced. During all the manipulations, the temperature was kept between 0° and 5° C. After the infusion was completed, the solution was slightly acidified with diluted HCl and extracted with ether. After drying, the ether was distilled off; 17.5 gm. (89.7 percent of theoretical) of α-cyano-γ-chloroacetoacetic ester was obtained.

EXAMPLE 2

4.7 gm (0.205 gm-At) of Na was dissolved in 70 ml of methanol and reacted with 19.5 gm (0.1 mole) of γ-bromoacetoacetic methyl ester. Subsequently, a solution of 10.6 gm. (0.1 mole) of BrCN was added dropwise to 40 ml of ether. The temperature was kept between 0° and 5° C. The processing was the same as stated in Example 1. The yield was 20.4 gm. of α-cyano-γ-bromoacetic acid methyl ester, which is 92 percent of theoretical.

EXAMPLE 3

10.0 gm. (0.05 mole) of copper acetate was dissolved hot in 150 ml of $H_2O$ and added to a solution of 19.1 gm. (0.1 mole) of γ-chloroacetoacetic acid diethyl amide in 150 ml of benzene. After brief stirring the green benzene solution was separated and dried over $MgSO_4$. Then 6.2 gm. (0.1 mole) of ClCN were introduced into the benzene solution — the temperature was kept at 20° to 30° C. The precipitated $CuCl_2$ was filtered off and the benzene solution was precipitated. 14.2 gm of α-cyano-γ-chloroacetoacetic acid dimethylamide was obtained, which corresponds to 65.6 percent of theoretical.

What is claimed is:

1. Process for the production of an α-cyano-γ-halo acetoacetic compound of the general formula:

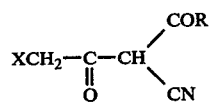

wherein X is halogen R is $-NR_1R_2$, $-NHR_3$ or $-O-R_4$, $R_1$ and $R_2$ are each alkyl having 1 to 18 carbons, or $R_1$ and $R_2$ form a morpholino or piperidino heterocyclic group with the N in $-NR_1R_2$, $R_3$ is alkyl having 1 to 18 carbon atoms or aryl, and $R_4$ is alkyl having 1 to 10 carbon atoms or aryl, which comprises:
 (a) reacting an alkali metal alcoholate and the haloacetoacetic compound of the formula:

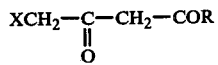

wherein X and R are the same as defined above, a metal salt of the haloacetoacetic compound of the formula:

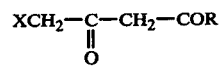

wherein X are R are the same as defined above and wherein the metal in the metal salt is an alkali metal, resulting; and
 (b) reacting said metal salt of said haloacetoacetic compound and a halo cyanogen in an inert solvent.

2. Process as claimed in claim 1 wherein the alkali metal alcoholate is formed from an alkali metal and an alcohol.

3. Process as claimed in claim 2 wherein the alkali metal is sodium and the alcohol is ethanol or methanol.

4. Process as claimed in claim 1 wherein the halo cyanogen is inserted into the reaction mixture containing the resultant metal salt without isolating the resultant metal salt from the reaction mixture.

5. Process as claimed in claim 1 wherein an ester or amide of the haloacetoacetic compound of the formula:

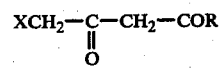

wherein X and R are the same as defined in claim 36, is dissolved in benzene or toluene, and the resultant solution is admixed with an aqueous metal salt solution, the metal salt of the haloacetoacetic compound of the formula:

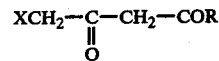

resulting.

6. Process as claimed in claim 1 wherein the reaction is conducted at a temperature of −10° to +40° C.

7. Process as claimed in claim 1 wherein the metal in said metal salt is sodium, potassium or rubidium.

8. Process as claimed in claim 7 wherein the metal is sodium.

9. Process as claimed in claim 1 wherein X is chlorine or bromine.

10. Process as claimed in claim 1 wherein said halo cyanogen is cyanogen fluoride, cyanogen chloride or cyanogen bromide.

11. Process as claimed in claim 10 wherein said halo cyanogen is cyanogen chloride.

12. Process as claimed in claim 1 wherein said solvent is an alcohol, toluene, benzene or ether.

13. Process as claimed in claim 12 wherein said solvent is an alcohol.

14. Process as claimed in claim 1 wherein $R_1$ is an alkyl having 1 to 18 carbon atoms, $R_3$ is an alkyl having 1 to 18 carbon atoms and $R_4$ is an alkyl having 1 to 10 carbon atoms.

* * * * *